United States Patent [19]

Meijer et al.

[11] Patent Number: 5,364,758
[45] Date of Patent: Nov. 15, 1994

[54] PRIMERS AND PROCESS FOR DETECTING HUMAN PAPILLOMAVIRUS GENOTYPES BY PCR

[75] Inventors: Christophorus J. Meijer, Leiden; Adrianus J. van den Brule, 's-Hertogenbosch; Jan M. Walboomers, Amsterdam; Petrus Snijders, Amstelveen, all of Netherlands

[73] Assignee: Stichting Researchfonds Pathologie, Amsterdam, Netherlands

[21] Appl. No.: 910,288

[22] PCT Filed: Jan. 18, 1991

[86] PCT No.: PCT/NL91/00009

§ 371 Date: Jul. 16, 1992

§ 102(e) Date: Jul. 16, 1992

[87] PCT Pub. No.: WO91/10675

PCT Pub. Date: Jul. 25, 1991

[30] Foreign Application Priority Data

Jan. 19, 1990 [NL] Netherlands .................. 9000134

[51] Int. Cl.$^5$ .................. C12Q 1/70; C07H 21/04; C12P 19/34
[52] U.S. Cl. .................................. 435/5; 435/6; 435/91.2; 536/24.32; 536/24.33; 935/78
[58] Field of Search .................. 435/5, 6, 91, 91.2; 536/23.72, 24.33, 77.78

[56] References Cited

U.S. PATENT DOCUMENTS 4,800,159 1/1989 Mullis .................. 435/172.3
5,182,377 1/1993 Manos .................. 536/24.32

FOREIGN PATENT DOCUMENTS 8806634 9/1988 WIPO.
8902934 4/1989 WIPO.
9002821 3/1990 WIPO.

OTHER PUBLICATIONS

Seedorf et al Virology (1985) 145:181–185.
Krawczyk et al Anal Biochem (1987) 165: 20–27.
Dartmann et al Virol (1986) 151: 124–130.
Williams Biotechnqies (1989) 17: 762–768.
Cole and Streeck, *Genome Organization and Nucleotide Sequence of Human Papillomavirus Typr 33 Which is Associated with Cervical Cancer*, Journal of Virology, Jun. 1986, pp. 991–995.
E. Schwarz et al., *DNA Sequence and Genome Organization of Genital Human Papillomavirus Type 6b*, The EMBO Journal, vol. 2, No. 12, 1983, pp. 2341–2348.

*Primary Examiner*—Margaret Parr
*Assistant Examiner*—Carla Myers
*Attorney, Agent, or Firm*—Cooper & Dunham

[57] ABSTRACT

The invention relates to primers and a method of detecting human papilloma virus (HPV) genotypes by means of the Polymerase Chain Reaction (PCR). The invention provides such primers and such PCR conditions that in principle any genital HPV genotype is detected. The general primers according to the invention consist of an oligonucleotide which comprises at the 3' end one of the sequences of SEQ ID NO: 3–6, or a sequence which is homologous to one of these four sequences as to at least 75%. In order to obtain amplification even in the case of a limited number of mismatches, in the PCR a relatively low annealing temperature of 30°–50° C. and a relatively high $Mg^{+2}$ concentration of 2–10 mM are used. The invention enables a sensitive and reliable preselection of samples to be examined, such as cervical smears.

16 Claims, No Drawings

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GCMCAGGGWC ATAAYAATGG                            20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

CGTCCMARRG GAWACTGATC                            20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TTTGTTACTG TGGTAGATAC                            20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GAAAAATAAA CTGTAAATCA 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TGGTACAATG GGCATATGAT 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

AATGGCTTTT GGAATTTACA 20

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

ACAGGATCCT TTGTTACTGT GGTAGATAC 29

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

ACAGGATCCG AAAAATAAAC TGTAAATCA 29

( 2 ) INFORMATION FOR SEQ ID NO:9:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

ACAGAATCCT TTGTTACTGT GGTAGATAC          29

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

ACAGAATCCG AAAAATAAAC TGTAAATCA          29

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

ACAAAGCTTT TTGTTACTGT GGTAGATAC          29

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

ACAAAGCTTG AAAAATAAAC TGTAAATCA          29

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:13:

ACAGGATCCT GGTACAATGG GCATATGAT   29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:14:

ACAGGATCCA ATGGCTTTTG GAATTTACA   29

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:15:

ACAGAATCCT GGTACAATGG GCATATGAT   29

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:16:

ACAGAATCCA ATGGCTTTTG GAATTTACA   29

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO ( x i ) SEQUENCE DESCRIPTION: SEQ ID NO:17:

ACAAAGCTTT GGTACAATGG GCATATGAT  29

( 2 ) INFORMATION FOR SEQ ID NO:18:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

ACAAAGCTTA ATGGCTTTTG GAATTTACA  29

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

ATGGTGATGT ACACAACACC  20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

GTAGTTGCAG GACAACTGAC  20

PRIMERS AND PROCESS FOR DETECTING HUMAN PAPILLOMAVIRUS GENOTYPES BY PCR

The invention relates to primers and primer pairs for use in a polymerase chain reaction (PCR) for amplification of DNA of genital human papillomavirus (HPV) genotypes. The invention also relates no a method for amplification of genital EPV DNA and a method of analysing a sample, such as a cervical smear,. for the presence of genital HPV genotypes.

At present, testing for cervical carcinoma and pre-stages thereof is mostly done by the detection of morphologically abnormal cells in cell smears of the cervix. This involves staining of smears by means of the Papanicoloau technique. By means of a light microscope, the pathologist detects premalignant and malignant cells. Then morphologically abnormal cells are classified into PAP classes I-V according to the severity of the cell lesion. With PAP I, only normal cells are found, while with PAP V, actual cancer cells are observed. This cytomorphological method, however, has some inherent disadvantages. In addition to great inter-observer variations, abnormal cells may be missed by "sample error" or by the microscopist. Furthermore, the PAP III class poses many problems as regards the gynaecological policy no be followed. With PAP III, which is found quite frequently, cancer may develop in the course of time, but persistence or regression to the normal condition may also occur. For this reason, therefore, there is a great need for better prognostic markers for cervical carcinoma.

In recent years, a great deal of research has been done into the causes of cervical carcinoma. This has revealed in particular the implication of the sexually transmittable human papiilomavirus (HPV). To date, 24 types of this virus have been associated with lesions of the cervical mucosa. The distinction between these HPV types is based on a difference in the base-sequence of the HPV DNA. Broadly, a 50% difference in base-sequence has been found to exist between the various HPV types. Studies have shown that the HPV types 6 and 11 are found in particular in benign genital lesions such as genital verrucae and in normal to mild dysplastic smears. These are called "low-risk" HPV types. HPV types 16 and 18 in particular and to a lesser extent 31, 33 and 35 occur in severely dyspiastic and "malignant" cervical smears (PAP IIIa higher) and are accordingly called "high-risk" HPV types. As yet, fairly little is known about the other 18 genital HPV types. It looks like the early detection of the various HPVs in cervical smears may in the future be an important prognostic factor in predicting the biological behaviour of cervical cells.

At present, there are various methods to determine the various human papillomavirus genotypes. The most sensitive method is the polymerase chain reaction (PCR), sometimes referred to as DNA amplification method, which in principle is capable of detecting one HPV DNA molecule in a smear. In this method, to a clinical sample (in this case a cervical smear), after an isolation of the DNA present therein (or in the case of the present invention, optionally after a short pretreatment) under specific conditions, 2 small synthetic pieces of single-stranded DNA, whose base-sequence is complementary to a part of one of the two strands of a given HPV genotype, are added. These DNA pieces, called primers, in virtue of their base-sequence, flank one HPV type-specific DNA fragment (the target DNA) of some 100 to 500 bases, in such a way that the enzyme Taq DNA polymerase present in the reaction mixture starts on the two primers and synthesizes the two strands in overlapping direction. The product obtained is called "amplimer". The procedure in which the target is synthesized once is called a cycle. Such a HPV-specific cycle comprises three steps, each taking place at a different temperature: the HPV target DNA is denatured at 94° C. (1 min), followed by a primer annealing step at 58° C. (2 min) and polymerization at 72° C. (1.5 min). By repeating such a cycle 30–40 times, the number of amplimers increases by a factor $2^{30-40}$, so than an amount of HPV type-specific DNA of the order of nanograms is produced.

This method, however, also has a number of disadvantages, namely:

a) Due to its high sensitivity, there is a great chance that false-positive results are obtained. Various forms of contamination in particular play a role here. However, by a physical separation of the various amplification steps, special primer choice, use of special pipets and strict laboratory discipline, the contamination problem can be strongly reduced. See in this connection for example Van den Brule et al., 1989, the contends of which are incorporated herein by reference; in this article special primers are proposed which reduce the contamination problem.

b) With the PCR method, only HPV types can be detected for which primers are available, which means that the DNA base sequence has to be known. An the moment, the DNA base-sequence is known only of the genital HPV types 6, 11, 16, 18, 31 and 33. Detecting non-sequenced HPV types is an awkward problem which is directly associated with the principle of amplification method itself. The PCR method is in principle successful only when it is performed with two HPV genotype-specific primers (TS-PCR). Each HPV genotype has is own specific primers.

The primers are mostly selected using matrix-analysis computer programs, the search being for oligonucleotides (approximately 20 bases long) which are very specific for the various HPV genotypes. Investigations have shown than these specific sequences in the HPVs are located in all open reading frames (potential genes). It is therefore fairly easy select HPV type-specific primers and the HPV types 6, 11, 16, 18, 31 and 33 can be detected through PCR fairly easily. As noted hereinabove, in Van den Brule et al., 1989, primers are described which lead to a considerable reduction of the contamination risk, so-called anti-contamination primers. These are primers which flank the HPV cloning site of the HPV plasmids used in the laboratory. On account of the fact these plasmids are mostly cultured in great quantities, they form in principle an important source of contamination in the PCR. However, printers are used which flank the cloning site and hence are located at the two ends of the HPV insertion, the unintended presence of such plasmids in the PCR space will not be disturbing.

Efficient and reliable screening for the genital HPV genotypes, however, should provide answers to the following two questions:

1) Is there any HPV present in the sample (such as a smear)? 2) What specific HPV genotypes occur in the sample?

Since PCRs with HPV type-specific primers do not provide adequate answers to these two questions, ways have been searched for of using more general primers which would be capable of detecting a broad range of HPVs (multiple HPV genotypes) at the same time. Matrix analysis of all currently known HPV DNA sequences, however, does yield some regions in the HPV genome which occur in substantially all HPV genotypes, in particular in the two different genes E1 and L1, but it has turned out that no set of oligonucleotides of approximately 20 base pairs can be found which occurs in all HPV genotypes whose sequence is known at this moment. Assuming that a successful PCR is wholly dependent on the availability of primers with perfect complementariness to their targets, it will be clear that special artifices are necessary to arrive at a general primer.

Manos et al., 1989, have circumvented this problem by using as primers a complex mixture of oligonucleotides. The primers described by them are the primers MY11 and MY09: 5'-GCMCAGGG-WCATAAYAATGG-3' (SEQ ID No.: 1) and 5'-CGTCCMARRGGAWACTGATC-3' (SEQ ID No.: 2), respectively. Because here M denotes both A and C, R both A and G, W both A and T and Y both C and T, each of these two primers consists of a mixture of different oligonucleotides. Thus, Manos et al. want to make sure that a primer pair suitable for each HPV genotype is present, i.e. with the complete complementariness between primers and target DNA that is considered requisite. The necessity of synthesizing such primer mixtures is one conspicuous drawback of this approach. However, a more important drawback is that as a result of use of a mixture, the concentration of the primers active for a given HPV type is considerably reduced, which causes a lower efficiency of the PCR. It has been found moreover that with these general primers a part of the existing HPV types are missed, in particular the important oncogenic type HPV-18.

Gregoire et al., 1989, have chosen a different road, namely the use of primers which contain an inosine-base in sites of variation between the different HPV genotypes, which base does not interfere with the hybridization. In order ensure nevertheless proper annealing and sufficient specificity at the same time, the primers must in practice be made longer than normal. These primers, too, leave yet to be desired as to their sensitivity.

Neither artifice described hereinabove provides a truly satisfactory solution to the problem referred to.

The present inventors have now found a solution that is satisfactory. Counter to the existing conviction that a successful PCR is determined by an essentially perfect complementariness between the primers and their targets, the inventors have devised two sets of primers with which both the genital HPV types whose sequence is known and genital HPV types whose sequence is as yet unknown, can be detected and in which the inherent mismatches to a maximum of 4 bases are yet accepted in the PCR. For the new primer sets to operate properly, however, it is highly recommended that slightly modified PCR conditions are employed, compared with the standard PCR, particularly as regards the $Mg^{2+}$ concentration and the annealing temperature.

In the first place the invention relates to a primer for use in a polymerase chain reaction (PCR) for amplifying DNA of genital human papiilomavirus (HPV) genotypes, consisting of an oligonucleotide which comprises at the 3'-end one of the following sequences:

| | |
|---|---|
| 5'-TTTGTTACTGTGGTAGATAC-3' | (SEQ ID NO:3) |
| 5'-GAAAAATAAACTGTAAATCA-3' | (SEQ ID NO:4) |
| 5'-TGGTACAATGGGCATATGAT-3' | (SEQ ID NO:5) |
| 5'-AATGGCTTTTGGAATTTACA-3' | (SEQ ID NO:6) | or a sequence which is homologous to one of these four sequences as to at least 75%, preferably as to at least 90%.

Primers according to the invention have a length of at least 20 bases or nucleotides. For practical reasons in particular, however, the primers will preferably not be longer than 40 nucleotides. The relatively shorter primers, such as those of exactly 20 bases, can be prepared more readily with a good yield; the relatively longer primers (i.e. primers with one of the sequences specified hereinabove at the 3'-end and an extension at the 5'-end), on the other hand, prove to act more efficiently in the PCR.

Preferred according to the invention is a primer for use in a PCR for amplifying DNA of genital HPV genotypes, consisting of an oligonucleotide of a length of 20–40 nucleotides which comprises at the 3'-end one of the following sequences:

| | |
|---|---|
| 5'-TTTGTTACTGTGGTAGATAC-3' | (SEQ ID NO:3) |
| 5'-GAAAAATAAACTGTAAATCA-3' | (SEQ ID NO:4) |
| 5'-TGGTACAATGGGCATATGAT-3' | (SEQ ID NO:5) |
| 5'-AATGGCTTTTGGAATTTACA-3' | (SEQ ID NO:6) |

The sequences indicated hereinabove consist of 20 bases or nucleotides. As stated, the invention comprises the possibility that the primers have a length of exactly 20 bases and hence consist of these specific sequences. Such primers are one of the preferred embodiments according to the invention: they consist of one of the following oligonucleotides, exactly 20 nucleotides long:

| | |
|---|---|
| 5'-TTTGTTACTGTGGTAGATAC-3' (SEQ ID NO:3) | (GP5) |
| 5'-GAAAAATAAACTGTAAATCA-3' (SEQ ID NO:4) | (GP6) |
| 5'-TGGTACAATGGGCATATGAT-3' (SEQ ID NO:5) | (GP1) |
| 5'-AATGGCTTTTGGAATTTACA-3' (SEQ ID NO:6) | (GP2) |

However, the primers may be extended at the 5' end to include additional sequences. Preferred are particularly primers of a length of more than 20 nucleotides, which comprise one or more restriction enzyme recognition sequences at the 5' end. Some examples of such preferred primers according to the invention are the following 29-nucleotide long oligonucleotides:

| | | |
|---|---|---|
| 5'-ACAGGATCCTTTGTTACTGTGGTAGATAC-3' | (SEQ ID NO:7) | (B-GP5) |
| 5'-ACAGGATCCGAAAAATAAACTGTAAATCA-3' | (SEQ ID NO:8) | (B-GP6) |
| 5'-ACAGAATCCTTTGTTACTGTGGTAGATAC-3' | (SEQ ID NO:9) | (E-GP5) |
| 5'-ACAGAATCCGAAAAATAAACTGTAAATCA-3' | (SEQ ID NO:10) | (E-GP6) |
| 5'-ACAAAGCTTTTTGTTACTGTGGTAGATAC-3' | (SEQ ID NO:11) | (H-GP5) |

-continued

| | | |
|---|---|---|
| 5'-ACAAAGCTTGAAAAATAAACTGTAAATCA-3' | (SEQ ID NO:12) | (H-GP6) |
| 5'-ACAGGATCCTGGTACAATGGGCATATGAT-3' | (SEQ ID NO:13) | (B-GP1) |
| 5'-ACAGGATCCAATGGCTTTTGGAATTTACA-3' | (SEQ ID NO:14) | (B-GP2) |
| 5'-ACAGAATCCTGGTACAATGGGCATATGAT-3' | (SEQ ID NO:15) | (E-GP1) |
| 5'-ACAGAATCCAATGGCTTTTGGAATTTACA-3' | (SEQ ID NO:16) | (E-GP2) |
| 5'-ACAAAGCTTTGGTACAATGGGCATATGAT-3' | (SEQ ID NO:17) | (H-GP1) |
| 5'-ACAAAGCTTAATGGCTTTTGGAATTTACA-3' | (SEQ ID NO:18) | (H-GP2). |

In practice the primers are employed as pairs. One primer pair according to the invention described here consists of a first oligonucleotide which at the 3' comprises the sequence 5'-TTTGTTACTGTGGTAGATAC-3' (SEQ ID No.: 3), or a sequence which is homologous to this sequence as to at least 75% (preferably at least 90%), and a second oligonucleotide which at the 3' end comprises the sequence 5'-GAAAAATAAACTGTAAATCA-3' (SEQ ID No.: 4), or a sequence which is homologous to this sequence as to at least 75% (preferably at least 90%), or consists of a first oligonucleotide which at the 3' end comprises the sequence 5'-TGGTACAATGGGCATATGAT-3' (SEQ ID No.: 5), or a sequence which is homologous to this sequence as to at least 75% (preferably at least 90%) and a second oligonucleotide which at the 3' end comprises the sequence 5'-AATGGCTTTTGGAATTTACA-3' (SEQ ID No.: 6), or a sequence which is homologous to this sequence as to at least 75% (preferably at least 90%).

More particularly, according to the invention a primer pair is preferred which consists of a first, 20–40 nucleotide-long oligonucleotide which at the 3' end comprises the sequence 5'-TTTGTTACTGTGGTAGATAC-3' (SEQ ID No.: 3), and a second, 20–40 nucleotide-long oligonucleotide which at the 3' end comprises the sequence 5'-GAAAAATAAACTGTAAATCA-3' (SEQ ID No.: 4), or consists of a first, 20–40 nucleotide-long oligonucleotide which an the 3' end comprises the sequence 5'-TGGTACAATGGGCATATGAT-3' (SEQ ID No.: 5), and a second, 20–40 nucleotide-long oligonucleotide which at the 3' (SEQ ID No.: 6) end comprises the sequence 5'-AATGGCTTTT-GGAATTTACA-3'.

Particularly preferred is such a primer pair consisting either of the oligonucleotide pair

5'-TTTGTTACTGTGGTAGATAC-3' (SEQ ID NO:3) (GP5), and
5'-GAAAAATAAACTGTAAATCA-3' (SEQ ID NO:4) (GP6)

or of the oligonucleotide pair

5'-TGGTACAATGGGCATATGAT-3' (SEQ ID NO:5) (GP1),
and
5'-AATGGCTTTTGGAATTTACA-3' (SEQ ID NO:6) (GP2).

Further preferred are primer pairs in which each of the two oligonucleotides is more than 20 nucleotides long and comprises one or more restriction enzyme recognition sequences an the 5'. As stated previously, it has been found that such primer pairs extended at the 5' end lead to a more efficient general primer (GP)-PCR. Examples of such primer pairs are the following oligonucleotide pairs:

| Res GP L1 | | | |
|---|---|---|---|
| 5'-ACAGGATCCTTTGTTACTGTGGTAGATAC-3' | (SEQ ID NO:7) | (B-GP5), | and |
| 5'-ACAGGATCCGAAAAATAAACTGTAAATCA-3' | (SEQ ID NO:8) | (B-GP6); | |
| 5'-ACAGAATCCTTTGTTACTGTGGTAGATAC-3' | (SEQ ID NO:10) | (E-GP5), | and |
| 5'-ACAGAATCCGAAAAATAAACTGTAAATCA-3' | (SEQ ID NO:10) | (E-GP6); | |
| 5'-ACAAAGCTTTTTGTTACTGTGGTAGATAC-3' | (SEQ ID NO:11) | (H-GP5), | and |
| 5'-ACAAAGCTTGAAAAATAAACTGTAAATCA-3' | (SEQ ID NO:12) | (H-GP6); | |
| Res GP E1 | | | |
| 5'-ACAGGATCCTGGTACAATGGGCATATGAT-3' | (SEQ ID NO:13) | (B-GP1), | and |
| 5'-ACAGGATCCAATGGCTTTTGGAATTTACA-3' | (SEQ ID NO:14) | (B-GP2); | |
| 5'-ACAGAATCCTGGTACAATGGGCATATGAT-3' | (SEQ ID NO:15) | (E-GP1), | and |
| 5'-ACAGAATCCAATGGCTTTTGGAATTTACA-3' | (SEQ ID NO:16) | (E-GP2); | |
| 5'-ACAAAGCTTTGGTACAATGGGCATATGAT-3' | (SEQ ID NO:17) | (H-GP1), | and |
| 5'-ACAAAGCTTAATGGCTTTTGGAATTTACA-3' | (SEQ ID NO:18) | (H-GP2). | |

B denotes a BamHI site, E denotes an EcoRI site, and H denotes a HindIII site.

On the 5' side the primers can in principle be extended with all restriction sites known to date. The BamHI, EcoRI and HindIII sites have merely been chosen here by way of example because they are the most common cloning sites.

These Res primers have an additional advantage in that the amplimers which are obtained in a Res GP-PCR can easily be cloned, for instance into the plasmid pBR322 and into plasmids derived therefrom, such as p. Gemini vectors. Thus the amplimers can be made suitable for conventional double-stranded sequencing (cloning capacity of 100 bp to several kb, The amplimers can also be cloned into the phage M13 (mp 18 and 19) for single-stranded sequencing (cloning capacity 100–500 bp). Owing to rapid developments in the field of sequencing techniques, direct sequencing of the amplimers is also one of the options. Direct sequencing of the amplimer products even seems to be the best identification for the virus. Res GP-PCR conditions are identical to the conditions described hereinbefore. With Res primers, the PCR products of HPV 13, 30, 32, 39, 45, 51 and seven as yet unknown HPVs have now successfully been analysed.

The invention is further embodied in a method of analysing a sample, such as a cervical smear, for the presence therein of genital human papillomavirus (HPV) genotypes by amplifying any DNA of a genital HPV that may be present in the sample by means of a polymerase chain reaction (PCR) and subsequently detecting it, using a primer pair according to the invention as defined hereinabove in the PCR.

According to the invention, during the primer annealing step, preferably a temperature of 30°–50° C. is used, more preferably a temperature of 35°–45° C., most preferably a temperature of 38°–42° C.

Further, according to the invention, preferably a $Mg^{2+}$ concentration of 2–10 mM is used, more preferably a magnesium ion ($Mg^{2+}$) concentration of 2.5–5 mM most preferably of 3.0–4.0 mM.

The optimum PCR conditions have been determined by means of tests in which some 14 different molecularly cloned HPV genotypes (pHPV 1a, 2a, 6b, 8, 11, 13, 16, 18, 30, 31, 32, 33, 45, 51) and control pBR322 DNA were used as targets in the GP-PCR. The optimum results were obtained at an annealing temperature of 40° C. (normally 58° C.) and a $Mg^{2+}$ concentration of 3.5 mM (normally 1.5 mM $Mg^{2+}$). The use of these conditions is preferred because that removes the extreme sensitivity from the method (1 to 100 HPV DNA molecules per sample). Thus a positive answer can be obtained to the question of the presence or absence of the biologically most important HPV types. False-negative results can thus be reduced to the very minimum. The conditions indicated (3.5 mM $Mg^{2+}$ and 40° C. annealing temperature) are therefore highly recommendable as standard conditions in a mass screening for genital HPV types with the general HPV primers according to the invention.

The new primer sets according to the invention enable the detection not only of the genital HPV types 6, 11, 16, 18, 31 and 33, whose sequence is already known, but also of the HPV types 13, 30, 45 and 51 whose sequence is (as yet) unknown and in all probability also of new HPV types.

Further, in view of the major importance of a screening for HPV genotypes in cervical smears, a general strategy for the screening of cervical smears has been set up, which is based on the use of HPV general primers according to the invention in combination with the previously described HPV type-specific anticontamination primers. The procedure of this new-designed PCR strategy, which makes use of general primers and HPV genotype-specific anticontamination primers, is as follows.

Protreatment of Cervical Smear

Cervical smears are placed in 5 ml phosphate buffered saline (PBS) with 0.05% merthiolate. The cell suspension is centrifuged at 3000 rpm (for instance in a Henrich centrifuge) for 10 min. The cell pellet is washed once in PBS and finally resuspended in 1 ml PBS and preserved until use at −20° C.

Experiments on a great number of smears, in which the results of a GP-PCR on frozen, thawed and boiled cell suspension were compared with the results of a GP-PCR on DNA which had been isolated from the same samples, revealed that the GP-PCR on samples which had undergone a freezing/thawing/boiling treatment yielded as much positivity as the GP-PCR on the isolated DNA. (See in this connection the articles by Van den Brule et al., 1990, the contents of which are considered incorporated herein by reference. ) This has considerable consequences. The GP-PCR can be performed faster because the protreatment steps associated with DNA extraction can be omitted. An even more important advantage is that the sample to sample contamination which is frequently encountered in DNA isolation of a larger series of samples, can be precluded. False-positive results are thereby avoided.

The preparation of the samples for the PCR preferably comprises thawing 1 ml cell pellet, proper vorcexing until a homogeneous suspension has been obtained, pipetting of 10 $\mu l$ suspension (preferably with special pipers with replaceable plungers and piper tips, such as the Microman type, Gilson, France), boiling for approx. 10 rain in a closed vessel, centrifugation of condensation (for instance in a Hetrich centrifuge) and adding a GP-PCR reaction mixture.

Performing GP-PCR

A total reaction mixture of 50 $\mu l$ is prepared comprising 10 $\mu l$ cell suspension; 50 mM KCl; 10 mM Tris HCl buffer pH 8.3; 0.01% (w/v) gelatin; 200 $\mu M$ of each dNTP; 3.5 mM $MgCl_2$; 50 pmol of a GP primer set according to the invention and 1 unit Taq DNA polymerase. Then follow application of a film of paraffin oil (1 drop) and incubation for 5 rain at 94° C. for the initial DNA denaturation. Then 40 cycli are performed (in a PCR processor) comprising 1 min at 94° C. (denaturation), 2 min at 40° C. (annealing), 1.5 min at 72° C. (polymerization). The last polymerization step is allowed to continue for 4 more minutes.

Analysis of PCR Reaction Products

After 40 cycli, 10 $\mu l$ of the PCR mixture is analysed through agarose gel electrophoresis. After this electrophoresis, the DNA fragments are transferred to a nylon merbrane (blotting) and hybridized with a general HPV probe. Such a general HPV probe may for instance consist of GP-PCR specific amplification products of cloned HPV 6, 11, 16, 18, 31 and 33. These amplimers can be isolated from low-melting agarose, fused and labeled using for instance the standard labeling method of random primer labeling. The membranes are hybridized (overnight) at $T_m-33$. After washing with $3\times SSC$, 0.5% SDS at 55° C., follows autoradiography (performed overnight).

The GP-PCR positive and doubtfully positive (very weak signals) samples are now afterscreened with a HPV type-specific PCR using anticontamination primers to identify specific sequenced HPV genotypes. In the GP-PCR positive smears that still remain then, HPV types whose sequence is (as yet) unknown, or new HPV types may occur, which are assessed for instance through dot blot analysis. This last dot blot analysis will in the future be required less and less often according as more HPV types are sequenced and qualify for the type-specific (TS) PCR.

This new strategy allows a screening of smears with most sensitive HPV detection method, wherein the problems attributable to contamination can be reduced to a minimum and a fast and reliable answer can be given to the question whether or not HPV is present in a smear.

The invention will be further explained and illustrated in and by the following examples.

EXAMPLES

Cell Cultures, Tissue Samples and HPV Clones

Use was made of the human cervical cancer cell lines CaSKi, Siha, C4-1 and HeLa 229. The first two contain HPV type 16, the other two contain HPV type 18 (Boshart et al., 1984; Schwarz et al., 1985; Yee et al., 1985). The cells were grown in Dulbecco's modified Eagle's medium, supplemented with 10% fetal calf's serum. After growth to near-confluence, cells were harvested by trypsinisation, washed with phosphate-buffered saline, centrifuged and then resuspended in 1 mM Tris-HCl, 1 mM EDTA pH 7.5.

Tissue samples of a laryngeal squamous-cell hyperplasia and a juvenile papilloma were retained after snap freezing until their use in liquid nitrogen. Their further treatment and the DNA extraction were carried out in accordance with standard procedures (Walboomers et al., 1988). Cervical smears were treated in the way as described by Van den Brule et al., 1989). The presence of HPV DNA in these samples was determined by Southern blot hybridization and PCR with HPV types 6-, 11-, 16-, 18- and 33-specific primers, as previously described (Van den Brule et al., 1989).

DNAs of different HPV types, cloned into pBR322 or into pUCl9 (pHPVs) were used as targets in a model system for an amplification controlled by general primers. In addition to a number of non-genital pHPVs the cloned genital HPV types 6b, 11, 13, 16, 18, 30, 31, 32, 33, 39, 45 and 51 were used.

Polymerase Chain Reaction

With a small modification, the PCR method described by Saiki et al., 1988 was used. The PCR was performed on 1 ng DNA of cloned pHPVs or on 100–500 ng of cellular DNA. also dilutions of different pHPV DNAs in 100 ng human placenta DNA or diluted Siha DNA were subjected to the PCR to determine the sensitivity of the assay. The reaction mixture of 50 μl also contained 50 mM KCl, 10 mM Tris-HCl pH 8.3, 0.01% (w/v) gelatin, 200 μM of each dNTP, $MgCl_2$ in a concentration of between 1.5 and 10 mM, 1 unit of a thermostable DNA polymerase (*Thermus aquaticus*, Cetus) and 50 pmol of each primer of the GP-5/GP-6 primer pair 5'-TTTGTTACTGTGGTAGATAC-3' (SEQ ID No.: 3) (GPS) and 5'-GAAAAATAAACTGTAAATCA-3' (SEQ ID No.: 4) (GP 6).

The mixture was overlaid with several drops of paraffin oil and incubated for 5 minutes at 94° C. for DNA denaturation, after which 40 cycli of amplification were performed using a PCR processor (Biomed). Each cycle comprised a denaturation step of 1 min at 94° C., an annealing step of 2 min at 40° C. and a chain-elongation step of 1.5 min at 72° C. To ensure the complete extension of the amplified DNA, each individual chain-elongation step was prolonged by 1 sac and the final chain-elongation step was prolonged by another 4 min. To prevent contamination by cloned pRPV DNA or PCR products, different steps, such as the preparations of samples and the amplification reactions, were conducted in strictly separated spaces. As negative controls, distilled water containing samples were used, none of which exhibited a successful amplification. Of each of the PCR mixtures, in the end a total of 10 μl was analysed by agarose gel electrophoresis.

Southern Blot Analysis of PCR Products

Electrophototically separated DNA fragments were transferred to nylon membranes (GeneScreen Plus, DuPont) by diffusion blotting in 0.5M NaOH, 0.6M NaCl. GP-5/GP-6 controlled, HPV-specific PCR products were used as probes after labeling with $^{32}p$ according to the random priming method. Hybridization was carried out at 65° C. ($T_m - 23°$ C., for high-stringent analysis) or 55° C. ($T_m - 33°$ C., for low-stringent analysis) in 0.5M sodium phosphate pH 7.4, 7% SDS, 1 mM EDTA for 16 h. Then washing was done at high ($T_m$) stringency in 0.1×SSC. (1×SSC is 0.15M NaCl and 0.015M sodium citrate), 0.5% SDS at 65° C. and at low ($T_m - 33°$ C.) stringency in 3×SSC, 0.5% SDS at 56° C. Autoradiography was performed for one day at −70° C. with Kodak Royal X-Omar film and intensifying screens.

Restriction Enzyme Analysis

Analysis of PCR products by treatment with restriction endonuclease was performed directly on a 10 μl sample of the reaction mixture, without prior purification and resuspension of the DNA in the recommended restriction buffer (Carman & Kidd, 1989). 2 Units of RsaI (Boehringer) were added and allowed to take effect for 2 h at 37° C. The products obtained were analysed on composite gels of 3% NuSieve agarose (FMC Bioproducts) and 1% type 1 agarose (Sigma) in order to obtain proper separation of DNA fragments of low molecular weight.

Dot Blot Analysis

For dot blot analysis, 1 μg pHPV DNA en pBR322 vector DNA were spotted onto nylon membranes (GeneScreen Plus; DuPont). As probes HPV-specific amplification products of 140 to 150 bp were used. The fragments were electrophoretically separated in low-melting agarose (Bio-Rad), excised from the gel and directly labeled by random primed labeling. The hybridization was carried out under high stringency, as described hereinabove. Then washing was done at high stringency ($T_m$) till 0.1×SSC, 0.5% SDS at 65° C. Autoradiography was carried out for a day at −70° C. with intensifying screens.

Computer Analysis and Primer Synthesis

All matrix, homology and restriction site analyses were performed with the Microgenie sequence analysis program [GenBank (Release No. 54), Beckman] developed by Queen & Korn, 1984.

The primers were synthesized on a DNA synthesizer (Applied Biosystems 380A) via the methoxy-phosphoramidite method.

Results

On the basis of the homology in parts of the E1 and L1 open reading-frames, observed in a matrix comparison of HPV types whose sequence is known, two pairs of oligomers were designed which could be used as general primer. Table A below shows the extent of agreement of the primers GP-5 and GP-6 with certain regions in the DNA (in the L1 open reading-frame) of the various HPV types.

TABLE A

| | | | number of mismatches |
|---|---|---|---|
| GP-5 | 5'-TTTGTTACTGTGGTAGATAC-3' | (SEQ ID NO:3) | |
| HPV-6b | . . . . . . . . . . . . . . . . . . . . | | 0 |
| HPV-11 | . . . . . . . . . . . . . . . . . . . . | | 0 |
| HPV-16 | . . . . . . . . . . . T . . T . . . . . | | 2 |
| HPV-18 | . . . . . . . . . . . . . . . . . . . . | | 0 |
| HPV-31 | . . . . . . . . . . . . . . . . . . . . | | 0 |
| HPV-33 | . . . . . . . . . . . . . . . . . . . . | | 0 |
| GP-6 | 5'-GAAAAATAAACTGTAAATCA-3' | (SEQ ID NO:4) | |
| HPV-6b | . . . . . . . . . . T . . . . . . . . . | | 1 |
| HPV-11 | . . . . . . . . . . . . . . . . . . . . | | 0 |
| HPV-16 | . . . . . . . . . . . . . . . . . . . . | | 0 |
| HPV-18 | . . . . . . . . . . . . . C . . . . . . | | 1 |
| HPV-31 | . . . . T . . . . . T . . . . . . . . . | | 2 |
| HPV-33 | . . . . . . C . . . . . . . . G . . . . | | 2 |

In Table A the dots denote identical bases; mismatches are specified. The nucleotide positions of the first nucleotides of the sequences matching GP-5/GP-6 are as follows:

| HPV Type | Nucleotide Numbers | Reference | Length of Region |
|---|---|---|---|
| HPV-6b | 6764/6902 | (Schwartz et al., 1983) | 139 bp |
| HPV-11 | 6749/6889 | (Dartmann et al., 1986) | 139 bp |
| HPV-16 | 6624/6765 | (Seedorf et al., 1985) | 142 bp |
| HPV-18 | 6600/6744 | (Cole & Danos, 1987) | 145 bp |
| HPV-31 | 6542/6683 | (Goldsborough et al., 1989) | 142 bp |
| HPV-33 | 6581/6719 | (Cole & Streeck, 1986) | 139 bp |

Table B shows the extent of agreement of the primers GP-1 and GP-2 with certain regions in the DNA (in the E1 open reading frame) of the different HPV types.

TABLE B

GP-1 5'-TGGTACAATGGGCATATGAT-3' (SEQ ID NO:5)
GP-2 5'-AATGGCTTTTGGAATTTACA-3' (SEQ ID NO:6)

| HPV Type | Number of Mismatches | | Nucleotide Numbers | Length of Region |
|---|---|---|---|---|
| | GP-1 | GP-2 | | |
| HPV-6b | 3 | 2 | 1913/2356 | 444 bp |
| HPV-11 | 2 | 4 | 1913/2356 | 444 bp |
| HPV-16 | 2 | 1 | 1942/2385 | 444 bp |
| HPV-18 | 1 | 4 | 2013/2456 | 444 bp |
| HPV-31 | 1 | 3 | 1890/2323 | 444 bp |
| HPV-33 | 1 | 3 | 1936/2379 | 444 bp |

The general primer pair GP-5/GP-6 was used in a PCR on 1 ng DNA of different pHPVs, under mildly-stringent conditions (3.5 mM $Mg^{2+}$). The PCR produces were detected by electrophoresis, UV-irradiation and ethidium bromide staining. The results (not shown) were that not only the HPV types 6b, 11, 16, 18, 31 and 33 with a sequence that is already known, but also the HPV types 13, 30, 32, 45 and 51, whose sequence is not as yet known, yielded PCR products of some 140 to 150 bp. In the case of the non-genital HPV types 1a, 2a and 8, the primer pair GP-5/GP-6 did not lead to DNA amplification, nor in control DNA, consisting of HinfI fragments of pBR322. The PCR products were therefore HPV-specific and not the result of a cross-reaction with vector-sequences. In some cases also amplified DNA with lower (40 to 45 bp) and higher molecular weight was observed, namely in the case of HPV-18, HPV-30 and HPV-32 DNA. The smaller DNA fragments seem to have been formed by ligation and amplification of the primers. The larger DNA fragments were probably the result of primer annealing on further target sequences within the HPV genome.

In order to determine the allowable number of mismatches between the primer sequences and the target DNA, the PCR was carried out under different stringent conditions by varying the $Mg^{2+}$ concentration, namely, 1.5, 2.5, 3.5 and 10 mM $MgCl_2$. The results (not shown here) were that 2 and 3 mismatches between primer and target DNA were accepted. The primer pair GP-5/GP-6 reacted with HPV-16 and HPV-33 under both high-stringent and low-stringent conditions. Partly on the evidence of a concurrently conducted investigation on general primers for non-Genital HPVs, it became clear that 4 mismatches are also allowable if low-stringent conditions are employed. PCR with the primer pair GP-5/GP-6 on DNA of the genital HPV-type 30, whose sequence is as yet unknown, gave rise to weak signals, which became stronger under lower-stringent conditions. Low-stringent conditions (10 μM $Mg^{2+}$) in the annealing step, however, also led to an increase in co-amplified DNA fragments.

The sensitivity of the GP-controlled PCR was determined by a study with different concentrations of pHPV DNA and Siha (HPV-16) DNA, diluted in human placenta DNA. The HPV-30 and HPV-33 DNA concentrations varied from 1 ng to 0.01 fg. Siha DNA, diluted in 100 ng human placenta DNA, was used in quantities of 10 ng to 1 pg. Annealing was done under moderate-stringency conditions (3.5 mM Mg2+). Hybridization of Southern blots was done under high-stringent conditions with GP PCR-amplified probes, specific for the HPV type in question (HPV in the case of Siha DNA). The results (not shown here) were that for pHPVs, which exhibited up to 3 mismatches with the primers, a detection level, as determined after hybridization of the PCR products with a GP-amplified homologous DNA probe, of 0.1 to 1 fg DNA was found, which corresponds with approx. 7 to 70 vital genomes. For HPV-30 a detection level between 10 fg and 1 pg pHPV DNA was determined, corresponding with some 700 to 70, 000 viral copies. Siha DNA could already be detected at 10 pg. Assuming than Siha cells contain 1–10 copies of HPV-16 DNA per genome and that a human diploid cell contains approx. 5 pg DNA, it can be derived from this that 2 to 20 copies of HPV-16 could be detected.

The type specificity of the PCR was determined by dot blot analysis. For this purpose, PCR products obtained with the primer pair GP-5/GP-6, of some 140 to 150 bp were isolated, labelled and hybridized under high-stringent conditions against a panel of pHPV DNA dots. The results (not shown here) showed that the PCR products were type-specific and did not result from contamination with other HPV types. Further analysis by treatment with the restriction enzyme RsaI confirmed the specificity of the PCR.

Using the primer pair GP-5/GP-6 the GP-PCR was also analysed for DNAs of cervical cancer cell lines, cervical smears and laryngeal lesions, which were well characterized by Southern blot analysis and PCR with HPV type-specific primers (Van den Brule et al., 1989). The PCR products were visualized both by electrophoresis, UV-irradiation and ethidium bromide staining, and by blotting and hybridization under low-stringent conditions with an amplified HPV type 16-specific PCR product. The results (not shown here) were that after agarose gel electrophoresis in most cases several bangs could clearly be observed and that a clear difference in detection level could be determined between high and low copy numbers of a given HPV type. From the DNA of the CaSki cell line, which contains more then 500 copies of EPV-16 per cell, a HPV-specific PCR product was formed which after electrophoresis appeared as a strong, well visible band. By contrast, the HPV product of the cell line Siha with a low HPV copy number C1 to 10 copies of HPV-16 per cell) appeared as a weak signal. Moreover, when Siha DNA was used as a targon, a number of other bands were obtained as well, whale the gel band pattern could hardly be distinguished from that of human placenta DNA or from that of a cervical smear which was negative for a broad range of HPVs. Identical results were found with HPV-18 containing HeLa cell line (10 to 50 copies of HPV-18 per cell) and C4-1 (1 to 5 copies of HPV-18 per cell), as well as with one of the cervical smears, a laryngeal papilloma (with a high concentration of HPV-6 DNA) and a hyperplasia (with a low concentration of RPV-6 DNA). For cervical smears with HPV-33, HPV-11, HPV-16 and HPV-18 DNA, too, PCR products were found. After blotting and low-stringent hybridization with a DNA probe amplified by means of GP-5/GP-6, specific for HPV-16, all HPV-specific fragments of 140–150 bp could be detected without inteference by the further bands.

Also on the evidence of experiments not further described here, it could be established in summary that the PCR technique using as primers the general primer pairs GP-1/GP-2 and GP-5/GP-6 proved capable of amplifying the cloned HPV types 6, 11, 13, 16, 18, 30, 31, 32, 33, 45 and 51.

Diagnostic Investigation

To test the actual usefulness of the primers and the PCR based thereon, cervical smears from 196 women (aged 16–60 years) with a broad spectrum of gynaecological complaints were investigated. First a smear for routine cytological investigation was made. The smears were classified according to a slightly modified Pap classification (Vooijs, 1987). For HPV detection, the residual material from the first scrape and from a second smear was placed in 5 ml phosphane-buffered saline (PBS) with 0.05% merthiolate. The smears were subjected to vigorous vortexing and the suspension was centrifuged for 10 min at 3000 rpm. The cells were resuspended in 1.0 ml PBS, of which 0.5 ml was used for DNA extraction (Maniatis et al., 1982) and HPV detection.

Snap frozen tissues of 21 invasive cervical squamous cell carcinomas were serially sectioned on a cryostat. The first and last sections were hematoxylin-eosin stained and histologically analysed for the presence of neoplastic cells. DNA of the remaining sections was isolated according to standard procedures (Walboomers et al., 1988).

HPV Detection

HPV detection was performed on each sample according to three different PCR procedures, all based on the method of Saiki et al., 1988. The HPV general primer sees GP-1/GP-2 and GP-5/GP-6 described hereinabove were used in GP-PCRs on cervical smears and biopsies. A mixture of HPV 6, 11, 16, 18, 33 specific "anti-contamination" primers, flanking the plasmid cloning sites to prevent amplification of possibly contaminating cloned HPV types (Van den Brule et al., 1989) was used for type-specific PCRs (TS-PCR). For the recently sequenced HPV type 31, as specific cloning site flanking primers were used the oligonucleotides 5'-ATGGTGATGTACACAACACC-3' (SEQ ID No.: 19) (HPV 31.1) and 5'-GTAGTTGCAG-GACAACTGAC-3' (SEQ ID No.: 20) (HPV 31.2). All primers were synthesized on a Pharmacia LKB Gene Assembler Plus according to the methoxy-phosphoramidite method.

The GP-PCRs were carried out in the manner described hereinabove. The HPV target sequences were amplified in 50 $\mu$l reaction mixture, which contained 100–500 ng of the purified DNA, as well as 50 mM KCl, 10 mM Tris-HCl pH 8.3, 0.01% (w/v) gelatin, 200 $\mu$M of each dNTP, 3.5 mM MgCl$_2$, 1 unit of a thermostable DNA polymerase (*Thermus aquatuaticus*, Cetus) and 50 pmol of one of the primer sets GP-1/GP-2 and GP-5/GP-6. To promote an efficient and reproducible amplification, a mixture of the components was made before the DNA was added.

As described hereinabove, the mixture was overlaid with a few drops of paraffin oil (to prevent evaporation) and incubated for 5 min an 95° C. to denature the DNA, after which 40 cycli of amplification were carried out by means of a PCR processor (Biomed). Each cycle comprised a denaturation Step of 1 min at 94° C., an annealing step of 2 min at 40° C. and a chain elongation step of 1.5 rain at 72° C. To ensure complete extension of the amplified DNA, each individual elongation step was increased by 1 sec and the final chain elongation step was prolonged for another 4 min. Finally, 10 $\mu$l of each reactsion mixture was analysed by 1.5% agarose gel electrophoresis.

The TS-PCRs were carried out in the same manner, except that 1.5 mM MgCl$_2$, 25 pmol of each primer and an annealing temperature of 55° C. were used.

Southern Blot Analysis of PCR Products

The DNA was transferred from the gel to a nylon membrane (Biotrace, Gelman sciences, U.S.A.) by diffusion blotting overnight in 0.5N NaOH, 1.5M NaCl. Thereafter, the membrane was saturated with 2×SSC. The TS-PCR products were analysed with HPV type-specific internal oligonucleotides as described by Van den Brule et al., 1989. The analysis of the GP-PCR products was carried out with HPV type-specific PCR amplification products as probe. The GP-PCR specific amplification products of cloned HPV types 6, 11, 16, 18 and 33 were electrophoretically separated in low melting agarose (BioRad, U.S.A.), excised from the gel and directly labelled by random primer labeling.

The membranes were incubated for 2 h at 65° C. in a prehybridization solution (0.5M sodium phosphate, pH 7.4, 7% SDS, 1 mM EDTA). Hybridization was carried out at 55° C. under low stringency conditions ($T_m - 33°$ C.) with [$\alpha$-$^{32}$P] dCTP random primer labelled PCR products of HPV 6, 11, 16, 18 and 33 for the detection of homologous HPV sequences in the manner as described hereinabove. Then washing was done at low stringency ($T_m-33°$ C.) till 3×SSC, 0.5% SDS at 55° C. Further, washing was done at high stringency ($T_m$) till 0.1×SSC, 0.1% SDS an 65° C. to find the remaining HPV type-specific signals. Autoradiography was performed with Kodak Royal X-Omat film and intensifying screens overnight to 3 days.

Dot Blot Analysis of PCR Procycts

Biotrace nylon membranes were used for dot blot analysis of GP-PCR samples which proved HPV positive after low-stringent hybridization but were no longer positive after stringent washing. To 40 µl of the PCR product, 20 µl of 0.75N NaOH, was added after incubation for 5 min at 100° C. and dilution with 60µl of 0.25×SSC, 12 µl of the sample was placed on the membrane. The dot blots were saturated with 2×SSC and hybridized in the manner described hereinabove under high stringency conditions ($T_m-23°$ C.) with random primer labelled cloned HPV plasmids or the derived GP-PCR products. Then washing was done at high stringency ($T_m$) till 0.1×SSC, 0.1% SDS at 65° C.

Results

Genomic DNA of cytologically normal and dysplastic cells of cervical smears and of biopsies of cervical carcinomas was subjected to a PCR with GP E1 (primer pair GP-1/GP-2), GP L1 (primer pair GP-5/GP-6) and TS primers. After electrophoresis on a 1.5% agarose gel and ethidium bromide staining (the different pictures obtained are not shown here) PCR products were detected both for smears that were positive for one of the sequenced HPV types 6, 11, 16, 18 and 33, and for smears which contain as yen non-sequenced HPV genotypes and for HPV negative smears. The non HPV-specific cellular or viral PCR products are a result of the low-stringency conditions, employed to allow mismatches of 4 bases in the primer annealing step. However, to confirm HPV specificity and increase the sensitivity, all PCR products were subjected to Southern blot analysis. Under low-stringency hybridization conditions with labelled GP-PCR products, derived from the cloned HPV types 6, 11, 16, 18 and 33, of which the sequence is known, followed by low-stringency washing, both the sequenced and the non-sequenced HPV genotypes could be detected, while for the HPV negative samples no signals were detected anymore. After further washing under high-stringency conditions, only the PCR products of HPV 6, 11, 16, 18 and 33 proved to be visible; the signals of HPV-specific products derived from homologous genotypes which were not in the probe mixture, proved to have disappeared.

The above described specific HPV detection was confirmed by a TS-PCR and by further hybridization with internal oligonucleotide probes, as previously described by Van den Brule et al., 1989.

All GP-PCR positive samples which had to contain non-sequenced genital HPV genotypes on the basis of hybridization results, were further examined by dot blot analysis. As probes, cloned HPV types 1, 2, 8, 13, 30, 31, 32, 45 and 51 or their specific GP-PCR products were used. Some of these HPV types proved no be present in the cervical smears.

Table C presents an overall view of the information which the GP-PCR provided about the occurrence of HPV types in the samples.

TABLE C

| Cytology | Number of HPV-positive samples | | | |
|---|---|---|---|---|
| | GP-PCR[1] | E1-PCR | L1-PCR | TS-PCR[2] |
| normal (Pap I-II) | 21/83 (25%) | 20/83 | 21/83 | 12/83 (14%) |
| mild dysplasia (Pap IIIa) | 62/78 (80%) | 62/78 | 59/78 | 39/78 (50%) |
| severe dysplasia (Pap IIIb) | 21/24 (88%) | 21/24 | 19/24 | 16/24 (67%) |
| CIS[3] (Pap IV) | 10/11 (91%) | 10/11 | 10/11 | 7/11 (64%) |
| cervical carcinomas[4] | 19/21 (91%) | 18/21 | 18/21 | 19/21 (91%) |

[1]results of the GP E1-PCR and the GP L1-PCR.
[2]TS-PCR for HPV types 6, 11, 16, 18 and 33.
[3]carcinoma in situ, as confirmed by histology.
[4]biopsies; histological examination revealed the two HPV negative preparations did not contain any carcinoma cells.

Table C shows that the TS-PCR found only 14% of the cytologically normal smears to be HPV positive, while the GP-PCR according to the invention reached 25%. In mild and severe dysplasia, HPV detection was increased from 50% to 80% and from 67% to 88%, respectively, through the use of the GP-PCR according to the invention. The use of GP E1-PCR and GP L1-PCR led to comparable percentages.

Table D shows the distribution of the different HPV types. complaints, were examined. In the symptom-free population the so-called oncogenic HPV types 6, 18, 31 and 33 were present in 1.5% of the cytologically normal smears, while the overall HPV prevalence was 3.5%.

Significantly higher HPV prevalences of 7% (oncogenic HPVs) and 14% (total HPV) were found in cytologically normal cervical smears from the "gynaecological" patient population. It was found than 78% in this latter patient group with HPV 16 and 18 positive smears had a history of cervical pathology, in other words, had been treated for premalignant cervical lesions. In smears of the cytological classes PAP IIIa, PAP IIIb and PAP IV an overall HPV prevalence of 70%, 84% and 100% was found. In all squamous cell carcinomas (n=50) HPV was demonstrated. The frequency of HPV 16 and 18 increased from 41% in PAP IIIa no 94% in cervical carcinomas. Because a lower HPV prevalence was found in cytologically normal cervixes of women without a clinical-pathological history, those findings strongly indicate that HPV assessment in population screening for cervical cancer is an important tool for detecting women who are an risk of developing cervical cancer and prestages thereof.

REFERENCES

Boshart et al., EMBO J. 3, 1151–1157 (1984)
Carman & Kidd, J. Virol. Meth. 23, 277–290 (1989)
Cole & Danes, J. Mol. Biol. 193, 599–608 (1987)
Cole & Streeck, J. Virol. 58, 991–995 (1986)
Goldsborough et al., Virology 171, 306–311 (1989)
Gregoire et al., J. Clin. Microbiol. 27, 2660–2665 (1989)
Maniatis et al., Molecular Cloning: A Laboratory Manual. Cold Spring Harbor Laboratory, Cold Spring Harbor, N.Y. (1982)
Manos et al., Cancer Cells 7, 209–214 (1989)
Queen & Kern, Nucl. Ac. Res. 12, 581–599 (1984)
Saiki et al., Science 239, 487–491 (1988)
Schwarz et al., EMBO J. 2, 2341–2348 (1983)
Schwarz et al., Nature, London 314, 111–114 (1985)
Seedorf et al., Virology 145, 181–185 (1985)
Van den Brule et al., J. Meal. Virol. 29, 20–27 (1989)

Van den Brule et al., Int. J. Cancer 45, 644–649 (1990)
Van den Brule et al., J. Clin. Microbiol. 28, 2739–2743 (1990)
Vooijs, Ned. Tijdschr. Geneeskd. 131, 1662–1663 (1987)
Walboomers et al., Amer. C. Path. 131, 587–594 (1988)
Yee et al., Am. J. Path. 119, 361–366 (1985)

We claim:

1. A primer for use in a polymerase chain reaction for amplifying DNA of genital papillomavirus genotypes, consisting of an oligonucleotide having a length of 20–40 nucleotides consisting of at the 3'-end a sequence selected from the group consisting of:

5'-TTTGTTACTGTGGTAGATAC-3' (SEQ ID NO:3),
5'-GAAAAATAAACTGTAAATCA-3' (SEQ ID NO:4),
5'-TGGTACAATGGGCATATGAT-3' (SEQ ID NO:5), and
5'-AATGGCTTTTGGAATTTACA-3' (SEQ ID NO:6).

2. A primer pair for use in a polymerase chain reaction for amplification of DNA of genital human papillomavirus genotypes, consisting of:

a first oligonucleotide of 20–40 nucleotides consisting of at the 3' end the sequence 5'-TTTGTTACTGTGGTAGATAC-3-', (SEQ. ID NO.:3), and a second oligonucleotide of 20–40 nucleotides consisting of at the 3' end the sequence, 5'-GAAAAATAAACTGTAAATCA-3' (SEQ ID NO.: 4)

or consisting of:

a first oligonucleotide of 20–40 nucleotides consisting of at the 3' end the sequence, TGGTACAATGGGCATATGAT-3' (SEQ ID NO.: 5) and a second oligonucleotide of 20–40 nucleotides consisting of at the 3' end the sequence, 5'-

AATGGCTTTTGGAATTTACA-3; (SEQ ID NO: 6).

3. A primer according to claim 1 consisting of an oligonucleotide selected from the group consisting of:

| | |
|---|---|
| 5'-TTTGTTACTGTGGTAGATAC-3' (SEQ ID NO:3) | (GP5), |
| 5'-GAAAAATAAACTGTAAATCA-3' (SEQ ID NO:4) | (GP6), |
| 5'-TGGTACAATGGGCATATGAT-3' (SEQ ID NO:5) | (GP1), |
| 5'-AATGGCTTTTGGAATTTACA-3' (SEQ ID NO:6) | (GP2). |

4. A primer according to claim 1 consisting of an oligonucleotide of 20–40 nucleotides consisting of at the 5' end one or more restriction-enzyme recognition sequences and at the 3' end a sequence selected from the group consisting of:

| | |
|---|---|
| 5'-TTTGTTACTGTGGTAGATAC-3' | (SEQ ID NO:3), |
| 5'-GAAAAATAAACTGTAAATCA-3' | (SEQ ID NO:4), |
| 5'-TGGTACAATGGGCATATGAT-3' | (SEQ ID NO:5), |
| 5'-AATGGCTTTTGGAATTTACA-3' | (SEQ ID NO:6). |

5. A primer according to claim 4 consisting of a 29 nucleotide long oligonucleotide selected from the group consisting of:

| | | |
|---|---|---|
| 5'-ACAGGATCCTTTGTTACTGTGGTAGATAC-3' | (SEQ ID NO:7) | (B-GP5), |
| 5'-ACAGGATCCGAAAAATAAACTGTAAATCA-3' | (SEQ ID NO:8) | (B-GP6), |
| 5'-ACAGAATCCTTTGTTACTGTGGTAGATAC-3' | (SEQ ID NO:9) | (E-GP5), |
| 5'-ACAGAATCCGAAAAATAAACTGTAAATCA-3' | (SEQ ID NO:10) | (E-GP6), |
| 5'-ACAAAGCTTTTTGTTACTGTGGTAGATAC-3' | (SEQ ID NO:11) | (H-GP5), |
| 5'-ACAGGATCCTGGTACAATGGGCATATGAT-3' | (SEQ ID NO:12) | (H-GP6), |
| 5'-ACAGAATCCTGGTACAATGGGCATATGAT-3' | (SEQ ID NO:13) | (B-GP1), |
| 5'-ACAGGATCCAATGGCTTTTGGAATTTACA-3' | (SEQ ID NO:14) | (B-GP2), |
| 5'-ACAGAATCCTGGTACAATGGGCATATGAT-3' | (SEQ ID NO:15) | (B-GP1), |
| 5'-ACAGAATCCAATGGCTTTTGGAATTTACA-3' | (SEQ ID NO:16) | (E-GP2), |
| 5'-ACAAAGCTTTGGTACAATGGGCATATGAT-3' | (SEQ ID NO:17) | (H-GP1), and |
| 5'-ACAAAGCTTAATGGCTTTTGGAATTTACA-3' | (SEQ ID NO:18) | (H-GP2). |

6. A primer pair according to claim 2 consisting of the oligonucleotide pair

| | |
|---|---|
| 5'-TTTGTTACTGTGGTAGATAC-3' (SEQ ID NO:3) | (GP5), and |
| 5'-GAAAAATAAACTGTAAATCA-3' (SEQ ID NO:4) | (GP6), |
| or the oligonUcleotide pair | |
| 5'-TGGTACAATGGGCATATGAT-3' (SEQ ID NO:5) | (GP1), and |
| 5'-AATGGCTTTTGGAATTTACA-3' (SEQ ID NO:6) | (GP2). |

7. A primer pair according to claim 2 in which each of the two oligonucleotides has a length of 20 to 40 nucleotides and has one or more restriction-enzyme recognition sequences at the 5' end.

8. A primer pair according to claim 7 consisting of one of the following oligonucleotide pairs:

| | | |
|---|---|---|
| 5'-ACAGGATCCTTTGTTACTGTGGTAGATAC-3' | (SEQ ID NO:7) | (B-GP5), and |
| 5'-ACAGGATCCGAAAAATAAACTGTAAATCA-3' | (SEQ ID NO:8) | (B-GP6); |
| 5'-ACAGAATCCTTTGTTACTGTGGTAGATAC-3' | (SEQ ID NO:9) | (E-GP5), and |
| 5'-ACAGAATCCGAAAAATAAACTGTAAATCA-3' | (SEQ ID NO:10) | (E-GP6); |
| 5'-ACAAAGCTTTTTGTTACTGTGGTAGATAC-3' | (SEQ ID NO:11) | (H-GP5), and |
| 5'-ACAGGATCCTGGTACAATGGGCATATGAT-3' | (SEQ ID NO:12) | (H-GP6); |
| 5'-ACAGAATCCTGGTACAATGGGCATATGAT-3' | (SEQ ID NO:13) | (B-GP1), and |
| 5'-ACAGGATCCAATGGCTTTTGGAATTTACA-3' | (SEQ ID NO:14) | (B-GP2); |
| 5'-ACAGAATCCTGGTACAATGGGCATATGAT-3' | (SEQ ID NO:15) | (e-GP1), and |
| 5'-ACAGAATCCAATGGCTTTTGGAATTTACA-3' | (SEQ ID NO:16) | (E-GP2) and; |
| 5'-ACAAAGCTTTGGTACAATGGGCATATGAT-3' | (SEQ ID NO:17) | (H-GP1), and |
| 5'-ACAAAGCTTAATGGCTTTTGGAATTTACA-3' | (SEQ ID NO:18) | (H-GP2). |

9. A method of amplifying DNA of genital human papilloma virus (HPV) genotypes comprising performing a polymerase chain reaction (PCR) employing a primer pair according to claim 2.

10. A method of analyzing a sample for the presence therein of genital human papilloma virus (HPV) genotypes comprising amplifying DNA of a genital HPV present in the sample by means of a polymerase chain reaction employing a primer pair according to claim 2 and subsequently detecting the amplified DNA.

11. A method according to claim 10 further comprising a primer annealing step at a temperature of 30°–50° C.

12. A method according to claim 10 further comprising a primer annealing step at a temperature of 35°–45° C.

13. A method according to claim 10 wherein the polymerase chain reaction is performed using a magnesium ion ($Mg^{+2}$) concentration of 2–10 mM.

14. A method according to claim 10 wherein the polymerase chain reaction is performed using a magnesium ion ($Mg^{+2}$) concentration of 2.5–5 mM.

15. A method according to claim 10 further comprising a primer annealing step at a temperature of 38°–42° C.

16. A method according to claim 10 wherein the polymerase chain reaction is performed using a magnesium ion ($Mg^{+2}$) concentration of 3.0–4.0 mM.

* * * * *